US007011813B2

(12) United States Patent
Kuhar et al.

(10) Patent No.: US 7,011,813 B2
(45) Date of Patent: Mar. 14, 2006

(54) COCAINE RECEPTOR BINDING LIGANDS

(75) Inventors: Michael J. Kuhar, Baltimore, MD (US); Frank Ivy Carroll, Durham, NC (US); John W. Boja, Baltimore, MD (US); Anita H. Lewin, Chapel Hill, NC (US); Philip Abraham, Cary, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 258 days.

(21) Appl. No.: 10/155,012

(22) Filed: May 28, 2002

(65) Prior Publication Data

US 2002/0188003 A1 Dec. 12, 2002

Related U.S. Application Data

(63) Continuation of application No. 08/506,541, filed on Jun. 24, 1995, now abandoned, which is a continuation-in-part of application No. 08/436,970, filed on May 8, 1995, now Pat. No. 5,736,123, and a continuation-in-part of application No. 08/164,576, filed on Dec. 10, 1993, now Pat. No. 5,496,953, and a continuation-in-part of application No. 09/972,472, filed on Mar. 23, 1993, now Pat. No. 5,413,779, which is a continuation-in-part of application No. 07/792,648, filed on Nov. 15, 1991, now abandoned, which is a continuation-in-part of application No. 07/564,755, filed on Aug. 9, 1990, now Pat. No. 5,128,118.

(51) Int. Cl.
*A61K 51/00* (2006.01)
*C07D 451/02* (2006.01)

(52) U.S. Cl. .................... 424/1.85; 424/1.81; 546/125; 546/124

(58) Field of Classification Search .............. 424/1.81, 424/1.85, 1.89; 546/124, 125, 126, 127, 546/128, 129, 130, 131, 132
See application file for complete search history.

(56) References Cited

U.S. PATENT DOCUMENTS

| 3,813,404 | A | 5/1974 | Clarke et al. |
| 4,111,827 | A | 9/1978 | Thompson et al. |
| 5,116,543 | A | 5/1992 | Lentsch |
| 5,128,118 | A | 7/1992 | Carroll et al. |
| 5,186,921 | A | 2/1993 | Kung et al. |
| 5,374,636 | A | 12/1994 | Moldt et al. |
| 5,380,848 | A | 1/1995 | Kuhar et al. |
| 5,413,779 | A | 5/1995 | Kuhar et al. |
| 5,490,955 | A | 2/1996 | Hagan et al. |
| 5,496,953 | A | 3/1996 | Kuhar et al. |
| 5,554,626 | A | 9/1996 | Moldt et al. |
| 5,736,123 | A | 4/1998 | Carroll |
| 5,935,953 | A | 8/1999 | Kuhar et al. |
| 6,123,917 | A | 9/2000 | Carroll |
| 6,329,520 | B1 | 12/2001 | Carroll et al. |
| 6,358,492 | B1 | 3/2002 | Kuhar et al. |
| 6,531,483 | B1 | 3/2003 | Kuhar et al. |

FOREIGN PATENT DOCUMENTS

WO    WO 93/09814    5/1993

OTHER PUBLICATIONS

Reith et al., "Structural Requirements for Cocaine Congeners to Interact with Dopamine and Seratonin Uptake Sites in Mouse Brain and to Induce Stereotypical Behavior", Biochemical Pharmacology, vol. 35, No. 7, pp. 1123-1129, 1986.

Boja, et al., "High Potency Cocaine Analogs: Neurochemical, Imaging, and Behavioral Studies", The Neurobiology of Drug and Alcohol Addiction, vol. 654 of the *Annals of the New York Academy of Sciences* Jun. 28, 1992.

Balaster, et al., "Potent substituted-3β-phenltropane analogs of cocaine have cocaine-like discriminative stimulus effects", *Drug and Alcohol Dependence*, 29 (1991) 145-151, Elsevier Scientific Publishers Ireland Ltd.

Cline, et al., "Stimulus generalization from cocaine to analogs with high *in vitro* affinity for dopamine uptake sites", *Behavioural Pharmacology* (1992).3 113-116 Short Report.

Cline, et al., "Behavioral Effects of Novel Cocaine Analogs: A Comparison with *in Vivo* Receptor Binding Potency"[1,2], HE Journal of Pharmacology and Experimental Therapeutics, vol. 260, No. 3, 1992.

Australian Patent Office Examiner's first report received in corresponding application on Feb. 4, 2003.

F. Ivy Carroll, et al., Therapeutic Uses of nAChRs, Chemistry and Life Sciences, pp. 2-28, "Monoamine Transporter Binding, Locomotor Activity, and Drug Discrimination Properties of 3-(4-Substituted Phenyl) Tropane-2-Carboxylic Acid Methyl Ester Isomers", Sep. 2004.

F. Ivy Carroll, et al., J. Med. Chem., 2004, 47, pp. 296-302, "Synthesis, Monoamine Transporter Binding Properties, and Behavioral Pharmacology of a Series of 3β-(Substituted phenyl)-2β-(3'-substituted isoxazol-5-yl)tropanes".

Nida Res. Monogr. (MIDAD4, 03618595); 1990, vol. 96, "Drugs Abuse: Chem., Pharmacol., Immunol., AIDS", pp. 112-121, XP002116828, Research Triangle Inst., Research Triangle Park, 27709, NC, USA.

(Continued)

*Primary Examiner*—Michael Hartley
(74) *Attorney, Agent, or Firm*—Oblon, Spivak, McClelland, Maier & Neustadt, P.C.

(57) ABSTRACT

Tropane derivatives having a high binding affinity and selectivity for dopamine transporters bear, on the tropane backbone either a carboxylic ester or isoxazole moiety, as well as a substituted phenyl moiety. The compounds have utility both as pharmaceutical and as imaging agents, when one or more atoms are radioactive.

18 Claims, No Drawings

OTHER PUBLICATIONS

F.I. Carroll, et al., "Synthesis and ligand binding of 3,β.-(3-subsituted phenyl)-and 3β-(3,4-disubstituted phenyl)tropane-2β-carboxylic acid methyl esters", Med. Chem. Res. (McReeb, 10542523), 1991, vol. 1, No. 6, pp. 382-387, XP002116826, Research Triangle Inst., Research Triangle Park, 27709, NC, USA.

J. Med. Chem. (JMCMAR, 00222623), Mar. 20, 1992, vol. 35, No. 6, pp. 969-981, XP002116827, Research Triangle Inst., Research Triangle Park, 27709, NC, USA.

J. Med. Chem. (JMCMAR, 00222623), 1993, vol. 36, No. 20, pp. 2886-2890, XP002116829, Research Triangle Inst., Research Triangle Park, 27709, NC, USA.

P. Kotian, et al., J. Med. Chem., 1996, vol. 39, pp. 2753-2763, "Synthesis, Ligand Binding, and Quantitative Structure-Activity Relationship Study of 3β-(4'-Substituted phenyl)-2β-heterocyclic Tropanes: Evidence for an Electrostatic Interaction at the 2β-Position".

F.I. Carroll, et al., J. Med. Chem., 2004, vol. 47, pp. 296-302, "Synthesis, Monoamine Transporter Binding Properties, and Behavioral Pharmacology of a Series of 3β-(Substituted phenyl)-2β-(3'substituted isoxazol-5-yl)tropanes".

F.I. Carroll, et al., J. Med. Chem., 1995, vol. 38, pp. 379-388, "Cocaine and 3β-(4'-Substituted phenyl)tropane-2β-carboxylic Acid Ester and Amide Analogues. New High Affinity and Selective Compounds for the Dopamine Transporter".

F.I. Carroll, et al., J. Med. Chem., 2004, 47, pp. 6401-6409, Monamine Transporter Binding, Locomotor Activity, and Drug Discrimination Properties of 3-(4-Substituted-phenyl) tropane-2-carboxylic Acid Methyl Ester Isomers.

COCAINE RECEPTOR BINDING LIGANDS

PARENT APPLICATIONS

This application is a Continuation of U.S. patent application Ser. No. 08/506,541, filed on Jun. 24, 1995, now abandoned, which is a Continuation-In-Part of U.S. patent application Ser. No. 08/436,970, filed May 8, 1995, now U.S. Pat. No. 5,736,123 and U.S. patent application Ser. No. 08/164,576, filed Dec. 10, 1993, now U.S. Pat. No. 5,496,953. The latter application is in turn a Continuation-In-Part of U.S. patent application Ser. No. 07/792,648, filed Nov. 15, 1991, now abandoned, which is in turn a Continuation-In-Part of U.S. patent application Ser. No. 07/564,755, filed Aug. 9, 1990, now U.S. Pat. No. 5,128,118 and U.S. patent application Ser. No. 07/972,472, filed Mar. 23, 1993, now U.S. Pat. No. 5,413,779, based on PCT Application PCT/US91/05553, filed Aug. 9, 1991, now U.S. Pat. No. 5,413,979. The entire disclosure of U.S. Pat. Nos. 5,496,953, 5,413,779, 5,380,848 and 5,128,118 are incorporated herein by reference.

THE INVENTORS' PRIOR DISCLOSURES

The parent applications referenced above are directed to cocaine receptor binding ligands, which show enhanced affinity for binding to cocaine receptors, particularly dopamine transporter sites, although binding affinity is also high at serotonin transporters. These prior patents and patent applications are directed to compounds having the general formula:

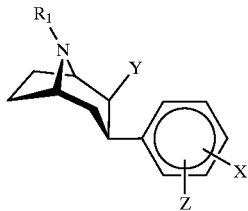

Wherein Y=$CH_2R_3$, $CO_2R_2$, $CONRR^1$, or

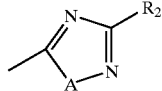

$R_1$=hydrogen, $C_{1-5}$ alkyl,
$R_2$=hydrogen, $C_{1-6}$ alkyl, $C_{3-8}$ cycloalkyl, $C_{1-4}$ alkoxy, $C_{1-6}$ alkynyl, halogen or amine,
$R_3$=OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl $OCOC_{1-3}$ alkylaryl,
A=S, O or N
X=H, $C_{1-6}$ alkyl, $C_{3-8}$ cycloalkyl, $C_{1-4}$ alkoxy, $C_{1-6}$ alkynyl, halogen, amino acylamido, and
Z=H, I, Br, Cl, F, CN, $CF_3NO_2$, $N_3$, $OR_1$, $CO_2NH_2$, $CO_2R_1$, $C_{1-6}$ alkyl, $NR_4R_5$, $NHCOF_5$, $NHCO_2R_6$,
wherein $R_4$–$R_6$ are each $C_{1-6}$ alkyl, R and $R^1$ are independently H, $C_{1-6}$ alkyl, $C_{1-6}$ alkene, $C_{1-6}$ alkyne, phenyl, phenyl substituted with 1–3 of $C_{1-6}$ alkyl, alkene, alkyl or alkoxy, $C_{1-6}$ alkoxy, phenoxy, amine, amine substituted with 1–2 of $C_{1-6}$ alkyl, alkene, alkyne, alkoxy or phenyl or phenoxy or R and $R^1$ may combine to form heterocyclic structure including pyrrolidinyl, piperidinyl and morpholino moieties, unsubstituted or substituted with 1–2 $C_{1-6}$ alkyl, alkene, alkyne or alkoxy groups.

As is reflected in the parent applications and patents, due to the high binding affinity of these compounds, particularly as measured against the compound of the literature [$^3$H]WIN 35,428 binding inhibition, these compounds have found particular use in both positron emission tomography (PET) as well as single photon emission computed tomography (SPECT). For PET use, one of the carbons of the molecule should be an [$^{11}$C] labeled form, while SPECT imaging may employ a radioactive halogen label, such as the molecule on the phenyl ring of the general formula, either X or Z of the above-described general formula. In particular, the radioactive labels $^{123}$I, $^{125}$I and $^{131}$I may be used.

As this art has developed, it has proved difficult to determine what particular substitutions on the tropane backbone will yield high binding affinities while remaining pharmaceutically acceptable. The applicant has now discovered a new family of tropane derivatives, characterized by an aryl ring substituent, and either an isoxazole substituent or a carboxylic ester substituent. These particular compounds have been demonstrated to have a high dopamine transporter binding efficiency, and a high selectivity.

SUMMMARY OF THE INVENTION

Compounds of the general formula:

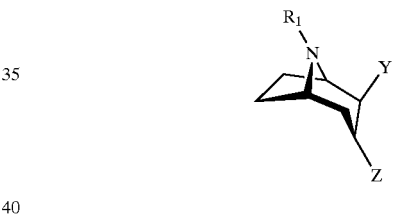

Wherein $R_1$ is hydrogen, $C_{1-5}$ alkyl
$R_a$ is phenyl, $C_{1-6}$ alkyl, $C_{1-6}$ alkyl-substituted phenyl
$R_b$ is $C_{1-6}$ alkyl, phenyl, $C_{1-6}$ alkyl substituted phenyl and
Z is phenyl or naphtyl bearing 1–3 substituents selected from the group consisting of F, Cl, I, $C_{1-6}$ alkyl, each substituent may be or include a radioactive label, fall within the scope of this invention.

These compounds have been demonstrated to have particular high binding affinity and selectivity for dopamine transporter sites.

The compounds of the invention can be prepared according to the methodologies established in the parent applications, incorporated herein by reference. The method of making the compound, per se, does not constitute an aspect of the invention. Particular measures for preparation of the isoxazole derivatives are shown herein. Nonetheless, other methods of making the compounds will occur to those of ordinary skill in the art, without the exercise of inventive faculty.

3β-(4'-Chlorophenyl)-2β-(3'-phenylisoxazol-5-yl)tropane) (4,RTI-177)Hydrochloride A soloution of n-butyl lithium in hexane (2.4M, 4.2 mL, 10.4 mmol) was added to a stirred solution of acetophenone oxime (0.703 g, 5.2 mmol) in a dry THF (10 mL) at 0° C. under nitrogen. After 1 h, a soloution of 3β-(4-chlorophenyl)tropane-2β-carboxylic acid methyl ester (1.18 g, 4 mmol) in dry THF (8 mL) was added, and the solution was allowed to warm to room temperature over 18 h. The mixture was poured into a stirred solution of concentrated sulfuric acid (2.28 g) in THF (12 mL) and water (2.8 mL) and was heated under reflux for 1 h. The cooled solution was basified using saturated aqueous potassium carbonate (10 mL) and extracted with 3×10 mL methylene chloride. The combined organic layer was dired and filtered. Removal of solvent under vacuum gave 1.46 g solid. Purification of the solid by flash column chromatography [20% (ether:triethylamine 9:1) in hexane] gave 0.75 g (50%) of pure 4 which was further purified by recrystallizing from ether:petroleum ether. $^1$H NMR (CDCl$_3$) § 1.74 (m, 3), 2.22 (m, 3), 2.27 (s, 3), 3.24 (m, 2), 3.36 (m, 2), 6.80 (s, 1), 6.94 (m, 2), 7.12 (m, 2), 7.40 (m, 3), 7.76 (m, 2). IR (CHCl$_3$) 2940, 1600, 1590, 1490, 1405, 1350 cm$^{-1}$.

The hydrochloride salt had mp 287° C. (dec); $[\alpha^2{}_{D3}$ −97.5 (c 0.28, CH$_3$OH). $^1$H NMR (CH$_3$OD) α 2.35 (m, 6), 2.84 (s, 3), 3.73 (m, 1), 4.09 (m, 1), 4.21 (s, 1), 7.14 (m, 4), 7.34 (m, 3), 7.57 (m, 2).

Anal. Calcd for C$_{23}$H$_{24}$Cl$_2$N$_2$O.0.25H$_2$O: C,H,N.

3α-(4'-Chlorophenyl)-2α-(5'-phenyl-1',3',4'-oxadiazol-2'-yl)tropane(5,RTI-188)Hydrochloride To 0.59 g (2 mmol) of 8 in 2 mL of POCl$_3$ was added 1.1 eq. of benzoic hydrazide, and the solution was reluxed under N$_2$ for 2 h. The reaction miscture was cooled and poured into ice and basified to pH 7–8 using conc. NH$_4$OH. To the aqueous layer was added 10 mL brince followed by extraction with 3×10 mL methylene chloride. The combined organic layer was dried (NaSO$_4$), filtered, andthe solvent removed in vacuo to give 0.9 g residue. PUrification of this residue by flash column chromatography [50% (ether:triethylamine 9:1) in hexane gave 0.33 g (42%) of pure 5 which was recrystallized from ether:petroleum ether.

Scheme

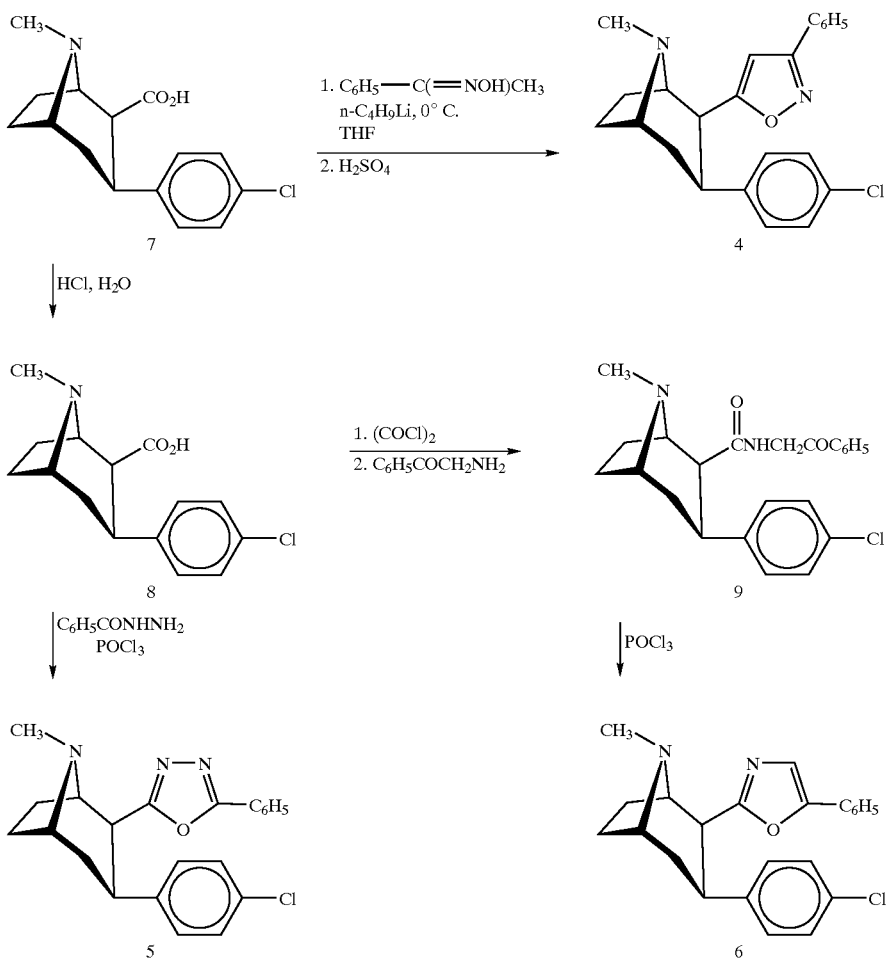

Well-established protocols for determining binding efficiency have shown selected compounds, pictured below, to have particularly high binding affinity, and selectivity, for dopamine transporter sites.

Highly Potent and Selective Analogs for the Dopamine Transporter
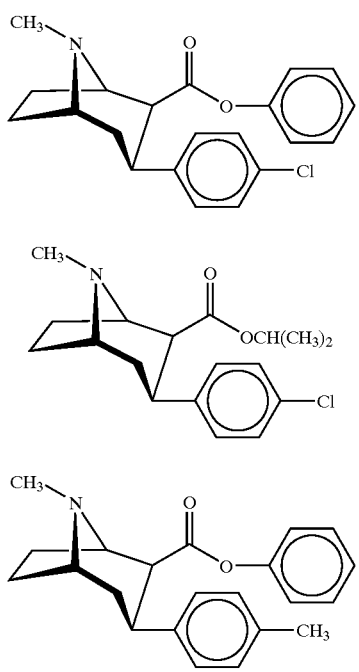
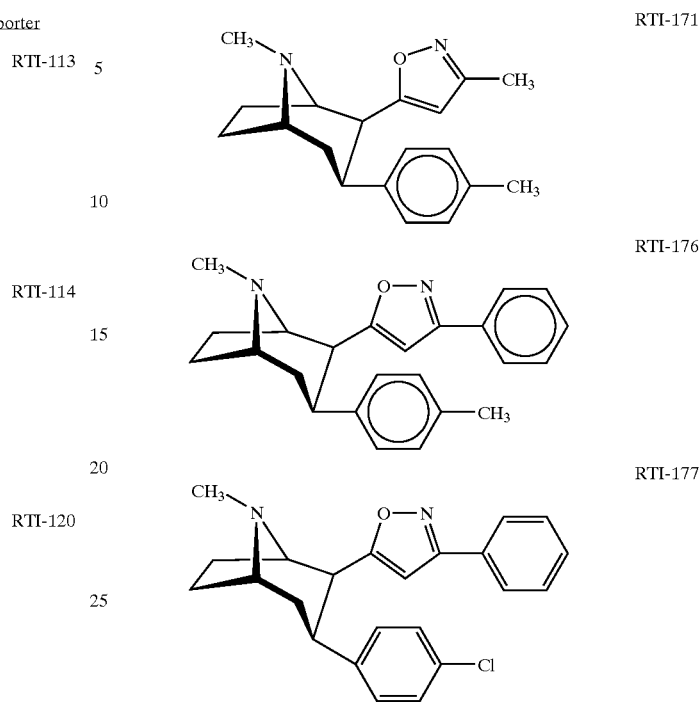
Comparison of Transporter Binding Potencies for
Selected 3β-(4-Substituted Phenyl)tropan-2β-carboxylic Acid Methyl Esters
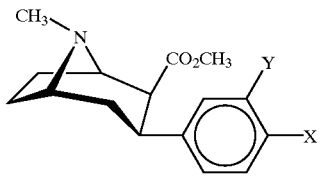
| | | | IC$_{50}$(nM) | | | | |
|---|---|---|---|---|---|---|---|
| RTI No. | X | Y | DA [$^3$H]WIN 35,428 | NE [$^3$H]Nisoxetine | 5-HT [$^3$H]Paroxetine | NE/DA Ratio | 5-HT/DA Ratio |
| WIN 35,065-2 | H | H | 23 | 920 | 1962 | 40 | 85 |
| WIN 35,428 | F | H | 13.9 | 835 | 692 | 60 | 50 |
| RTI-32 | CH$_3$ | H | 1.71 | 60 | 240 | 35 | 140 |
| RTI-31 | Cl | H | 1.12 | 37 | 44.5 | 33 | 40 |
| RTI-55 | I | H | 1.26 | 36 | 4.21 | 29 | 3.3 |
| RTI-51 | Br | H | 1.69 | 37.4 | 10.6 | 22 | 6 |
| RTI-88 | NH$_2$ | I | 1.35 | 1329 | 120 | 984 | 89 |
| RTI-111 | Cl | Cl | 0.79 | 17.96 | 3.13 | 67 | 4 |
| RTI-112 | Cl | CH$_3$ | 0.81 | 36.2 | 10.5 | 45 | 13 |
| RTI-318 | | | 0.51 | 21.1 | 0.80 | 41 | 1.6 |

3β-(4'-Methylphenyl)-2β-(heterocyclic)tropane
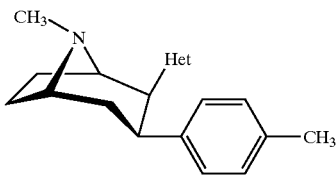
| | | IC$_{50}$(nM) | | | | |
|---|---|---|---|---|---|---|
| RTI No. | Het | DA [$^3$H]WIN 35,428 | NE [$^3$H]Nisoxetine | 5-HT [$^3$H]Paroxetine | NE/DA Ratio | 5-HT/DA Ratio |
| 151 | 3-C$_6$H$_5$, 5-CH$_3$-1,2,4-oxadiazole | 2.33 | 60 | 1074 | 26 | 461 |
| 171 | 3-CH$_3$, 5-CH$_3$ isoxazole | 0.93 | 254 | 3818 | 273 | 410 |
| 176 | 3-C$_6$H$_5$, 5-CH$_3$ isoxazole | 1.58 | 398 | 5110 | 252 | 3234 |
| 178 | 2-CH$_3$, 5-C$_6$H$_5$ oxazole | 35.4 | 677 | 1699 | 19 | 48 |
| 194 | 2-CH$_3$, 5-CH$_3$-1,3,4-oxadiazole | 4.45 | 253 | 4885 | 57 | 1098 |
| 195 | 2-C$_6$H$_5$, 5-CH$_3$-1,3,4-oxadiazole | 47.48 | 1310 | 22,310 | 28 | 470 |
| 199 | 2-C$_6$H$_5$, 5-CH$_3$-1,3,4-thiadiazole | 35.88 | 24,320 | 51,460 | 678 | 1434 |

3β-(4'-Chlorophenyl)-2β-(heterocyclic)tropanes
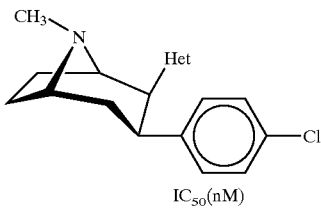
IC$_{50}$(nM)
| RTI No. | Het | DA [$^3$H]WIN 35,428 | NE [$^3$H]Nisoxetine | 5-HT [$^3$H]Paroxetine | NE/DA Ratio | 5-HT/DA Ratio |
|---|---|---|---|---|---|---|
| 130 | 3-C$_6$H$_5$-1,2,4-oxadiazol-5-yl | 1.62 | 244.6 | 195 | 151 | 120 |
| 188 | 5-C$_6$H$_5$-1,3,4-oxadiazol-2-yl | 12.6 | 930 | 3304 | 74 | 262 |
| 200 | 5-C$_6$H$_5$-1,3,4-thiadiazol-2-yl | 15.3 | 4142 | 18,416 | 271 | 1203 |
| 165 | 3-CH$_3$-5-methylisoxazol-5-yl | 0.59 | 181 | 572 | 307 | 970 |
| 177 | 3-C$_6$H$_5$-isoxazol-5-yl | 1.28 | 504 | 2418 | 394 | 1889 |
| 189 | 5-C$_6$H$_5$-oxazol-2-yl | 19.7 | 496 | 1116 | 25 | 57 |
| 219 | 5-C$_6$H$_5$-thiazol-2-yl | 5.71 | 8563 | 10,342 | 1500 | 1811 |
| 202 | benzothiazol-2-yl | 1.37 | 403 | 1119 | 294 | 817 |
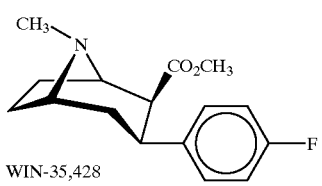
WIN-35,428
IC$_{50}$(nM)
| DA | 5-HT | NE |
|---|---|---|
| 14 | 156 | 85 |
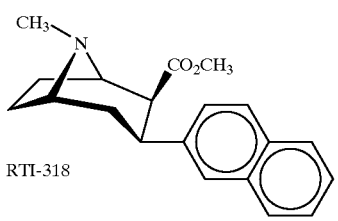
RTI-318
IC$_{50}$(nM)
| DA | 5-HT | NE |
|---|---|---|
| 0.51 | 0.80 | 21 |

-continued

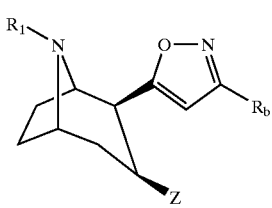

| IC$_{50}$(nM) | | | IC$_{50}$(nM) | | |
|---|---|---|---|---|---|
| DA | 5-HT | NE | DA | 5-HT | NE |
| 21 | 5062 | 1231 | 1.1 | 11.4 | 70.2 |

It should be noted that the compounds described and claimed herein are not useful solely as imaging compounds. The compounds are useful as surrogate agonists for treatment of cocaine abuse, as well as abuse of other psychostimulant drugs including amphetamines. The compounds of this invention exhibit a very slow onset of action, as well as a very long duration of action. Both of these attributes are desirable for appropriate substitute medication for psychostimulant abuse.

These compounds, because of their selectivity for the dopamine transporter are useful as antagonist drugs, or blockers of the actions of cocaine or other psychostimulants, blocking psychostimulant access but not inhibiting the functioning of the transporter. Further, treatment of neurodegenerative disorders may be affected through potentiation of neurotransmitter action. The compounds of the invention may be used to inhibit re-uptake in such situations. Finally, these compounds may find utility as analgesics. Accordingly, the compounds have utility in both their labeled and unlabeled forms.

This invention has been disclosed in terms of generic formula, as well as by specific example. Where examples are set forth, they are not intended, and should not be interpreted, as limiting. In particular, isomeric forms, as well as alternate substituents will occur to those of ordinary skill in the art without the exercise of inventive faculty, and remain within the scope of the invention, which is unlimited save by the recitation of the claims below.

What is claimed is:

1. A 2,3-cis substituted binding ligand having high binding affinity and selectivity for dopamine transporters, having the formula:

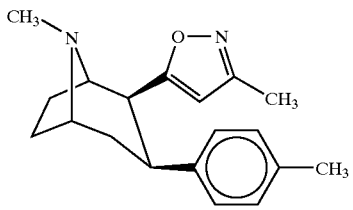

wherein $R_1$ is hydrogen or $C_{1-5}$ alkyl;

$R_b$ is $C_{1-6}$ alkyl, phenyl, or $C_{1-6}$ alkyl-substituted phenyl; and

Z is phenyl or naphthyl bearing 1–3 substituents selected from the group consisting of Cl, I, and $C_{1-6}$ alkyl, and wherein each substituent may be or include a radioactive label.

2. The binding ligand of claim 1, wherein $R_1$ is hydrogen.

3. The binding ligand of claim 1, wherein $R_1$ is $C_{1-5}$ alkyl.

4. The binding ligand of claim 1, wherein $R_b$ is $C_{1-6}$ alkyl.

5. The binding ligand of claim 1, wherein $R_b$ is phenyl.

6. The binding ligand of claim 1, wherein $R_b$ is $C_{1-6}$ alkyl-substituted phenyl.

7. The binding ligand of claim 1, wherein Z is phenyl bearing 1–3 substituents selected from the group consisting of Cl, I, and $C_{1-6}$ alkyl, and wherein each substituent may be or include a radioactive label.

8. The binding ligand of claim 7, wherein each substituent is not and does not include a radioactive label.

9. The binding ligand of claim 7, wherein each substituent is or includes a radioactive label.

10. The binding ligand of claim 1, wherein Z is napthyl bearing 1–3 substituents selected from the group consisting of Cl, I, and $C_{1-6}$ alkyl, and wherein each substituent may be or include a radioactive label.

11. The binding ligand of claim 10, wherein each substituent is not and does not include a radioactive label.

12. The binding ligand of claim 10, wherein each substituent is or includes a radioactive label.

13. The binding ligand of claim 1, of the formula:

-continued

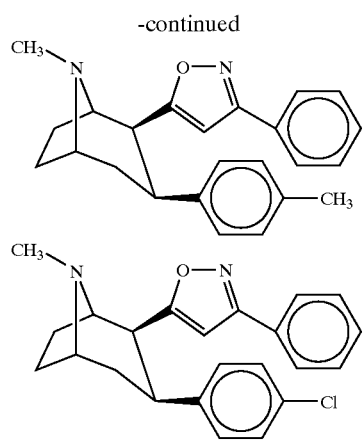

14. The binding ligand of claim 1, wherein said binding ligand bears a radioactive label selected from the group consisting of $^{11}$C, $^{123}$I, $^{125}$I, and $^{131}$I.

15. The binding ligand of claim 4, wherein Z is phenyl substituted by $C_{1-6}$ alkyl.

16. The binding ligand of claim 15, wherein Z does not include a radioactive label.

17. The binding ligand of claim 6, wherein Z is Cl.

18. The binding ligand of claim 15, wherein Z is not a radioactive label.

* * * * *

UNITED STATES PATENT AND TRADEMARK OFFICE
CERTIFICATE OF CORRECTION

PATENT NO. : 7,011,813 B2
APPLICATION NO. : 10/155012
DATED : March 14, 2006
INVENTOR(S) : Michael J. Kuhar et al.

Page 1 of 1

It is certified that error appears in the above-identified patent and that said Letters Patent is hereby corrected as shown below:

Column 4, Line 5:
"4.21 (s, 1), 7.14 (m, 4)" should read --4.21 (m, 1), 6.12 (s, 1), 7.14 (m, 4)--.

Signed and Sealed this

Ninth Day of January, 2007

JON W. DUDAS
*Director of the United States Patent and Trademark Office*